United States Patent
Umehara et al.

(10) Patent No.: US 7,985,878 B2
(45) Date of Patent: Jul. 26, 2011

(54) METHOD FOR REMOVING IODIDE COMPOUND FROM ORGANIC ACID

(75) Inventors: Yoichi Umehara, Yokohama (JP);
Takeshi Minami, Yokohama (JP);
Susumu Yamamoto, Yokohama (JP);
Haruto Kobayashi, Yokohama (JP);
Yasuo Hosono, Yokohama (JP)

(73) Assignee: Chiyoda Corporation, Yokohama-shi (JP)

( * ) Notice: Subject to any disclaimer, the term of this patent is extended or adjusted under 35 U.S.C. 154(b) by 144 days.

(21) Appl. No.: 12/441,476

(22) PCT Filed: Jun. 29, 2007

(86) PCT No.: PCT/JP2007/063513
§ 371 (c)(1),
(2), (4) Date: Mar. 16, 2009

(87) PCT Pub. No.: WO2008/038446
PCT Pub. Date: Apr. 3, 2008

(65) Prior Publication Data
US 2009/0259072 A1 Oct. 15, 2009

(30) Foreign Application Priority Data
Sep. 25, 2006 (JP) ................... 2006-258437

(51) Int. Cl.
*C07C 51/42* (2006.01)
(52) U.S. Cl. ...................................... 562/608
(58) Field of Classification Search .......... None
See application file for complete search history.

(56) References Cited

U.S. PATENT DOCUMENTS

| | | | |
|---|---|---|---|
| 5,801,279 A | 9/1998 | Miura et al. | |
| 6,657,078 B2 * | 12/2003 | Scates et al. | 562/519 |

FOREIGN PATENT DOCUMENTS

| | | |
|---|---|---|
| EP | 0196173 A1 | 10/1986 |
| EP | 0296584 A2 | 12/1988 |
| EP | 0484020 A2 | 5/1992 |
| EP | 0535605 A | 4/1993 |
| EP | 0687662 A2 | 12/1995 |
| JP | 2006-016349 A | 1/2006 |
| KR | 90-006072 B1 | 10/1986 |
| WO | 00/56454 A | 9/2000 |

OTHER PUBLICATIONS

Kun et al, Journal of Polymer Science: Part C, The Pore Structure of Macroreticular Ion Exchange Resins, 1967, 16, pp. 1457-1469.*
International Search Report of PCT/JP2007/063513, Mailing Date of Oct. 18, 2007.
Korean Office Action dated Jan. 10, 2011, issued in corresponding Korean Patent Application No. 10-2009-7005147.
Japanese Office Action date Feb. 2, 2011, issued in corresponding Japanese Patent Application No. 2006-258437.

* cited by examiner

*Primary Examiner* — Paul A Zucker
(74) *Attorney, Agent, or Firm* — Westerman, Hattori, Daniels & Adrian, LLP

(57) ABSTRACT

An iodide compound is adsorbed and removed from an organic acid containing the iodide compound as an impurity by passing the organic acid through a packed bed of a cation-exchange resin having silver ion carried thereon at 50° C. or lower. The cation-exchange resin is a macroporous-type resin with an average particle size of 0.3 to 0.6 mm and an average pore size of 15 to 28 nm, and silver ion substitutes for 40 to 60% of the active site.

3 Claims, 2 Drawing Sheets

METHOD FOR REMOVING IODIDE COMPOUND FROM ORGANIC ACID

TECHNICAL FIELD

The present invention relates to a method for removing an iodide compound from an organic acid. Particularly, the present invention relates to a method for refining acetic acid synthesized with a methanol carbonylation method, by removing an iodide compound contained therein.

BACKGROUND ART

A method for carbonylating methanol with carbon monoxide in the presence of a rhodium catalyst to produce acetic acid is well known as so-called "Monsanto method". There are two methods for the carbonylation method. One is a method in which acetic acid is used as a solvent, methanol of a raw material is added to the acetic acid, a rhodium compound as a catalyst is dissolved therein and a carbon monoxide gas is fed into the reaction mixture (homogeneous catalytic reaction). The other is a method in which a solid catalyst having a rhodium compound carried on a carrier is suspended in the reaction mixture instead of dissolving the rhodium compound into it (heterogeneous catalytic reaction). However, in both cases, an iodide compound such as methyl iodide is added into the reaction mixture as a cocatalyst (reaction promoter), so that about several tens to several hundreds of ppb (µg/kg) of the iodide compound remains in the acetic acid produced by the carbonylation method even after the acetic acid has been refined by distillation. The iodide compound remaining in the acetic acid in such a manner acts as a catalyst poison to a VAM (vinyl acetate monomer) synthetic catalyst when the acetic acid is used as a raw material of VAM for instance, and accordingly needs to be removed into a level of about several parts per billion.

There is a method for removing an iodide compound remaining in acetic acid by passing the acetic acid through a packed bed of a macroporous-type cation-exchange resin having silver ion or mercury ion exchanged and carried (Japanese Patent Publication No. H05-021031). This method is effective for efficiently removing the iodide compound from the acetic acid and decreasing the iodide concentration of outflowing acetic acid into 10 ppb or lower, but it has a problem that as the carbon number of the iodide compound increases, an adsorption rate decreases, a width of an adsorption zone is widened and a silver utilization at a breakthrough point decreases. As a result, the method can treat a small amount of acetic acid per unit resin volume, which is not favorable from the viewpoint of a treatment cost.

In order to solve the above described problem several methods have been investigated. One is a method in which an ion exchange resin having an active site only on a surface is used, which method is developed through having paid particular attention to the point that the diffusion of an iodide compound in adsorbent particles limits an adsorption rate (Japanese Patent Application Laid-Open No. H09-291058). Another one is a method in which an iodide adsorption apparatus is operated at a temperature higher than about 50° C. (Japanese Patent Application Laid-Open No. 2003-527963). However, the former method has a disadvantage that it is not easy to prepare an ion-exchange resin so as to have the active site only on the surface, and that if the inside of the ion-exchange resin particle is consequently not used effectively, an exchange capacity per unit volume of resin becomes small. On the other hand, the latter method has a disadvantage that when the apparatus is operated at a high temperature, the active site is more rapidly decomposed and released, and silver ion is also more rapidly released.

In addition, a method is proposed which starts an iodide removal operation at a low temperature, and every step of time when an iodide compound is detected in a discharged liquor due to decrease of an iodide removal rate, increases the temperature, so as to reduce the release of an active site and the release of silver ion (Japanese Patent Application Laid-Open No. H09-291059). However, the method also have a disadvantage that it is a complicated operation to increase the temperature step by step, and that the active site unavoidably decomposes and is released and silver ion is unavoidably released, because the exchange resin finally contacts with a high-temperature liquid by any means. The released active site and silver ion become impurities in a product of acetic acid, which is not preferable.

DISCLOSURE OF THE INVENTION

For this reason, such an adsorbent is demanded as to be able to maintain an adsorption rate that provides a sufficient silver utilization even without being operated at a high temperature which accelerates the release of an active site and silver ion. As a result of investigations by the present inventors, it was found that the release rates of the active site and silver ion exponentially increase as the treatment temperature increases from 40° C. to 70° C. Specifically, as the temperature increases by every 10° C., a silver ion leaching rate becomes about twice and an active site decomposition rate becomes about 10 times, as is shown in Table 1. When the temperature is 50° C. or lower in particular, the decomposition rate of the active site is 0.1% per year or less, which is in a negligible range, but when the temperature exceeds 50° C., the decomposition of the active site becomes not negligible.

Accordingly, an object of the present invention is to obtain a silver utilization equivalent to that in the case of passing the liquid at a temperature as high as over 50° C., even when passing the liquid at a temperature of 50° C. or lower, and preferably 40° C. or lower.

TABLE 1

| Treatment temperature (° C.) | Silver ion leaching rate (%/year) | Active site decomposition rate (%/year) |
|---|---|---|
| 40 | 0.06 | 0.01 |
| 50 | 0.12 | 0.1 |
| 60 | 0.23 | 1.0 |
| 70 | 0.46 | 10.0 |

The present invention provides a method for adsorbing/removing an iodide compound from an organic acid containing the iodide compound as an impurity by passing the organic acid through a packed bed of a cation-exchange resin having silver ion carried thereon at 50° C. or lower, wherein the cation-exchange resin is a macroporous-type resin with an average particle size of 0.3 to 0.6 mm, preferably 0.3 to 0.5 mm, more preferably 0.3 to 0.45 mm, and an average pore size of 15 to 28 nm, preferably 20 to 28 nm, and silver ion substitutes for 40 to 60%, preferably 50 to 60%, of the active sites, and thereby solves the above described problem.

A typical organic acid intended to be treated is acetic acid, and an iodide compound contained in the acetic acid as an impurity is mainly a lower alkyl iodide having 1 to 12 carbon atoms.

DETAILED DESCRIPTION OF THE INVENTION

Figure 1:
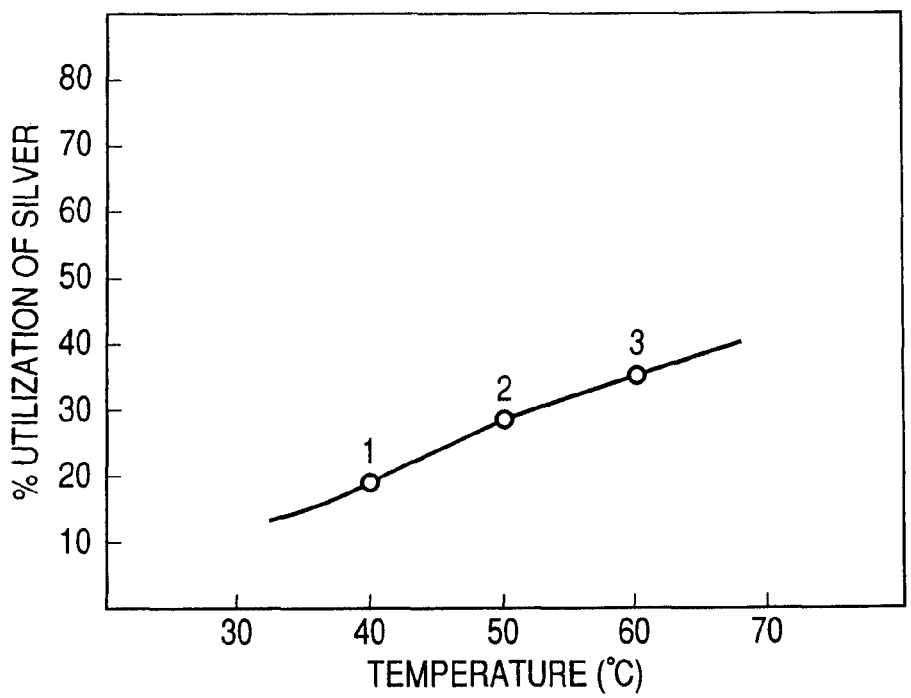
FIG. 1 shows a relationship between a silver utilization and a temperature of a passing liquid in the case of using a conventional adsorbent.

A cation-exchange resin is generally prepared by the steps of: preparing particles of styrene/divinylbenzene copolymer of a mother material, which is produced with the use of 4 to 20 wt. % of divinylbenzene as a crosslinking agent; and introducing a strongly-acidic sulfonate group into the particle as a cation-exchange group (active site). The generally used particulate ion-exchange resin normally has a particle size distribution in which particles with a particle size of 0.3 to 1 mm occupy 95% or more, and has an average particle size (diameter of 50% particles passing with wet sieving method) of about 0.5 to 0.8 mm.

A cation-exchange resin having been conventionally used for removing an iodide compound from an organic acid is a macroporous-type (macroreticular or MR type) resin having a large specific surface area originating in pores even in a dry state. In contrast to this, there is a gel-type resin which acquires pores produced only after having been immersed and swelled in water, but it cannot be preferably used because of being little swollen in the organic acid containing little water and not acquiring effective pores.

A macroporous-type resin forms macropores in itself by adding an immiscible solvent to itself in a polymerization step, and removing the solvent after the polymerization step. Thus formed macropores have an average pore size normally in a range of about 5 to 100 nm. The average pore size in the above description is determined from a BET specific surface area, apparent density and a value of true density, by the following expression.

$$d = (4 \times 10^3/S) \times (1/da - 1/ds)$$

d: average pore size (nm)
S: BET specific surface area (m$^2$/g)
da: apparent density (g/mL)
ds: true density (g/mL)

The present inventors examined a relationship between the average particle size and an adsorption rate for an iodide compound, through using macroporous-type cation-exchange resins with different average particle sizes, and making resins carry silver ion thereon to prepare adsorbents. As a result of this, the present inventors found that the adsorption rate for the iodide compound largely increases along with the decrease of the average particle size. It is generally expected that the adsorption rate increases by decreasing the particle size of the adsorbent, because an outer surface area per unit filled volume increases inversely proportionally to the particle size of the adsorbent. However, it cannot be always said that the conscious use of the resin with the small average particle size is advantageous, because even though the outer surface area increases a little, the pressure drop at the packed column filled with that resin also increases by decreasing the size of the resin. However, as a result of a detailed examination according to the present inventors, when having employed the adsorbent of the cation-exchange resin having silver ion carried thereon and having the decreased particle size and the external surface area 1.6 times larger than the adsorbent with a normal particle size, and having made the adsorbent adsorb the iodide compound, the adsorption rate for the iodide compound showed about twice the amount in the case of the adsorbent with the normal particle size, in an early stage of adsorption (when silver utilization was about 1%), about 2.9 times the amount when the silver utilization was about 20%, and about 12 times the amount when the silver utilization was 40%. The reason why such an unexpected result was obtained is not clear, but it is assumed that while silver iodide selectively precipitates around an outer surface of the adsorbent as the adsorption of the iodide compound proceeds, and the silver iodide precipitate obstructs the iodide compound from diffusing into pores and decreases the adsorption rate for the iodide compound, the increase in the outer surface area of the cation-exchange resin due to the decrease of the particle size effectively compensates the decrease.

A method according to the present invention is based on the above described knowledge obtained from the experiment, and is specifically a method for removing an iodide compound in an organic acid by the steps of: preparing an adsorbent having silver ion carried on a macroporous-type cation-exchange resin with an average particle size of 0.3 to 0.6 mm, preferably 0.3 to 0.5 mm, more preferably 0.3 to 0.45 mm; preparing an adsorption column filled with the adsorbent; and passing the organic acid containing the iodide compound as an impurity through the adsorption column. When the average particle size exceeds 0.6 mm, a sufficient adsorption rate is not obtained at 50° C. or lower, and when an average particle size is less than 0.3 mm, the pressure drop at the adsorption column increases. In order to obtain the cation-exchange resin with an average particle size of 0.3 to 0.6 mm, it is acceptable to remove large particles in a commercially available cation-exchange resin with a sieve, or to previously prepare a polystyrene resin with a small size and sulfonate it.

Any macroporous-type cation-exchange resin can be used without a problem in particular, as long as it is a strongly acidic resin having a sulfonate group as an ion exchange group. But, the macroporous-type cation-exchange resin having an extremely small average pore size tends to relatively reduce its adsorption capacity, because of increasing the resistance of an iodide compound in diffusing into the particles. On the other hand, the macroporous-type cation-exchange resin having an extremely large average pore size tends to relatively reduce its adsorption rate, because of reducing its specific surface area. Generally, the average pore size is preferably in a range of 15 to 28 nm, more preferably in a range of 20 to 28 nm. In addition, the macroporous-type cation-exchange resin with an extremely low cross-linking degree (for instance, 5% or less) intensely causes swell and shrink, and has poor physical strength, which are not preferable. In addition, a weakly acidic cation-exchange resin having a carboxyl group as an ion-exchange group is not preferable because carried silver ion tends to be released when the organic acid is passed through the resin.

It is recommended for making the cation-exchange resin carry silver ion to temporarily convert sulfonate groups in the resin completely into an acidic form (hydrogen form) by using a strong acid such as hydrochloric acid and sulfuric acid and then convert 40 to 60% of the total active sites in hydrogen form into a silver form by using an aqueous solution such as silver nitrate or silver acetate. When the silver form is less than 40%, the cation-exchange resin acquires a too small adsorption capacity for an iodide compound. By the way, the present inventors found that when the cation-exchange resin having more than 60% of the silver form adsorbs in iodide compound, for instance, at 40° C. (which is a typical treatment temperature anticipated in a method according to the present invention), the adsorption rate decreases. The present inventors assume the cause in the following way. Specifically, a mechanism in which an cation-exchange resin having silver ion carried thereon removes an iodide compound contained in acetic acid is considered to be that at first, the iodide compound is converted into hydrogen iodide and ester compounds through an esterification reaction while using an acid center (active site of acid form) of the cation-exchange resin as a catalyst, subsequently the hydrogen iodide reacts with silver ion to form silver iodide, and the iodide compound is thereby fixed on the adsorbent and removed from the product. In the process, when a treatment temperature is higher than 50° C., even a small amount of acid centers can provide a sufficient esterification reaction rate, but when the treatment temperature is 50° C. or lower, a large amount of acid centers need to be left in order to provide the sufficient esterification reaction rate. In brief, it is assumed that when the cation-exchange resin is highly substituted into a silver form, the resin has little acidic centers thereon, which decreases the esterification reaction rate for the iodide compound and also decreases the adsorption rate.

A cation-exchange resin having silver ion carried thereon is charged into an adsorption column for removing an iodide compound from an organic acid. A height of the packed bed shall be preferably about 1 to 5 times the diameter of the packed bed. A space velocity in a step of adsorbing and removing the iodide compound in the organic acid by passing the organic acid through the packed bed of the silver ion-carrying resin has to be within a condition conventionally used in general, and is normally a condition of LHSV=about 6 to 10 (which means that the quantity of the passing liquid per hour is 6 to 10 times the bed volume of the resin).

The temperature of the organic acid when passed through a packed bed of a silver ion-carrying resin shall be 50° C. or lower and preferably be 40° C. or lower. It is the most preferable to pass the liquid at about 40° C. As described above, when the temperature of the passing liquid exceeds 50° C., an active site (ion exchange group) of a resin and silver ion carried thereon are leached out more rapidly. A method according to the present invention employs a resin having a high adsorption rate, and accordingly effectively makes use of carried silver ion even at a low temperature of 50° C. or lower, and particularly about 40° C. in the treatment.

A method according to the present invention also has advantages of having a large removal capacity until the adsorption for an iodide compound reaches a breakthrough point and discharging a small amount of silver ion into the organic acid during treatment, which will be described later. The reason is considered such that while silver ion which had been carried on a resin but has temporarily been released into a liquid caused by solid-liquid equilibrium or the decomposition of the active site is again adsorbed by an ion exchange group of an acid form in a downstream side, the resin employed in the present invention has a large outer surface area because of having a small size, and rapidly re-adsorbs the silver ion.

EXAMPLES (1) Preparation of Adsorbent

Cation-exchange resins A to F shown below were prepared, and were used as base resins for preparing an adsorbent.

A. Cation-exchange resin AMBERLYST 15 made by Rohm and Haas Company (with average particle size of 0.68 mm and average pore size of 24 nm)

B. The above-described AMBERLYST 15 of which the average particle size was adjusted into 0.55 mm by screening C. Newly synthesized particulate cation-exchange resin by the present inventors (with average particle size of 0.42 mm and average pore size of 24 nm)

D. Newly synthesized particulate cation-exchange resin by the present inventors (with average particle size of 0.36 mm and average pore size of 24 nm)

E. Cation-exchange resin DIAION RCP160M (with average pore size of 10 nm) made by Mitsubishi Chemical Corporation, of which the average particle size was adjusted into 0.52 mm by screening F. AMBERLYST XH2071 (with average pore size of 30 nm) of which the average particle size was adjusted into 0.52 mm by screening An adsorbent was prepared by making the above described resins A to F carry silver ion so as to have a predetermined silver substitution rate (30 to 90%) with respect to the total ion-exchange capacity of the above each resin.

(2) Flow Test

In each flow test, an adsorbent in an amount of 5 mL prepared in the above described item (1) was filled in a column (10 mm$\phi$×100 mmH), and acetic acid containing 25 ppm decyl iodide ($C_{10}H_{21}I$) was passed through the column at a flowing rate of 60 mL/hour (LHSV=12). At this time, the inner temperature of an adsorption column was controlled by circulating warm water into the adjacent jacket outside the column. The concentration of decyl iodide in the effluent from the adsorption column was measured by a gas chromatography installed with an electron capture detector (ECD-GC), and a period of time until the concentration reaches 10 ppb was determined to be breakthrough time. In addition, an amount (by mole) of adsorbed decyl iodide was determined from a volume of a liquid passed through until the resin reaches the breakpoint, and the ratio of the adsorbed amount with respect to the amount (by mole) of carried silver ion was determined to be a silver utilization (%).

(2) Result

The result of a flow test is shown in Table 2.

TABLE 2

| RUN NO. | Base resin | Average particle size mm | Average pore size nm | Silver substitution rate % | Temperature of passing liquid ° C. | Breakthrough time hr | Silver utilization % |
|---|---|---|---|---|---|---|---|
| 1 | A | 0.68 | 24 | 50 | 40 | 144 | 18.9 |
| 2 | A | 0.68 | 24 | 50 | 50 | 216 | 28.4 |
| 3 | A | 0.68 | 24 | 50 | 60 | 264 | 34.7 |
| 4 | B | 0.55 | 24 | 50 | 40 | 456 | 55.6 |
| 5 | C | 0.42 | 24 | 50 | 40 | 552 | 72.5 |
| 6 | D | 0.36 | 24 | 50 | 40 | 552 | 72.6 |
| 7 | E | 0.52 | 10 | 50 | 40 | 312 | 41.0 |

TABLE 2-continued

| RUN NO. | Base resin | Average particle size mm | Average pore size nm | Silver substitution rate % | Temperature of passing liquid °C. | Breakthrough time hr | Silver utilization % |
|---|---|---|---|---|---|---|---|
| 8 | F | 0.52 | 30 | 50 | 40 | 288 | 37.9 |
| 9 | C | 0.42 | 24 | 30 | 40 | 216 | 45.0 |
| 10 | C | 0.42 | 24 | 40 | 40 | 360 | 59.2 |
| 11 | C | 0.42 | 24 | 70 | 40 | 720 | 67.6 |
| 12 | C | 0.42 | 24 | 90 | 40 | 840 | 61.3 |

The result of the above described test 1 (RUN NO. 1) to 3 are shown in FIG. 1. Numeric values noted upside the plotted data are run numbers. It is understood from FIG. 1 that when an adsorbent based on a resin with a normal average particle size is used for the test, a breakthrough time and a silver utilization depend on a temperature of a passing liquid, and when the temperature of the passing liquid is 50° C. or lower (tests 1 to 2), the silver utilization is less than 30% at the breakthrough point.

Figure 2:
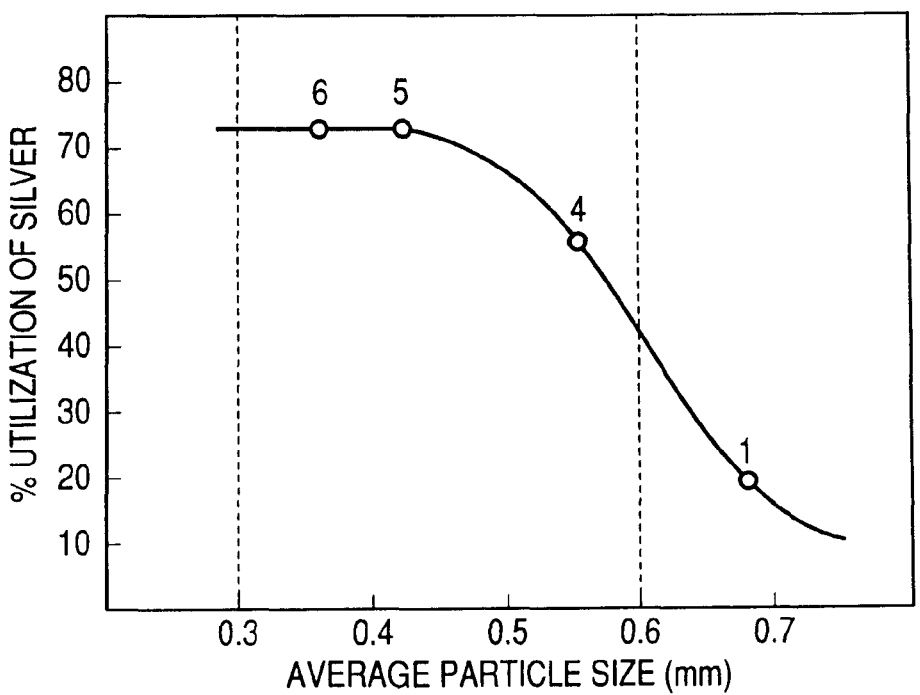
FIG. 2 shows a relationship between a silver utilization and an average particle size of adsorbents.

The result of the above described tests 4 to 6 and the test 1 are shown in FIG. 2. Numeric values noted upside the plotted data are run numbers. It is understood from FIG. 2 that when conditions other than the adsorbent size are the same, the breakthrough time and the silver utilization are largely increased by reducing an average size of resin particles. It is also understood that the silver utilization in the resin with the average particle size of 0.68 mm is greatly different from that of 0.55 mm, and that when the resin has an average particle size of 0.6 mm or smaller, the silver utilization is about 40% or more.

Figure 3:
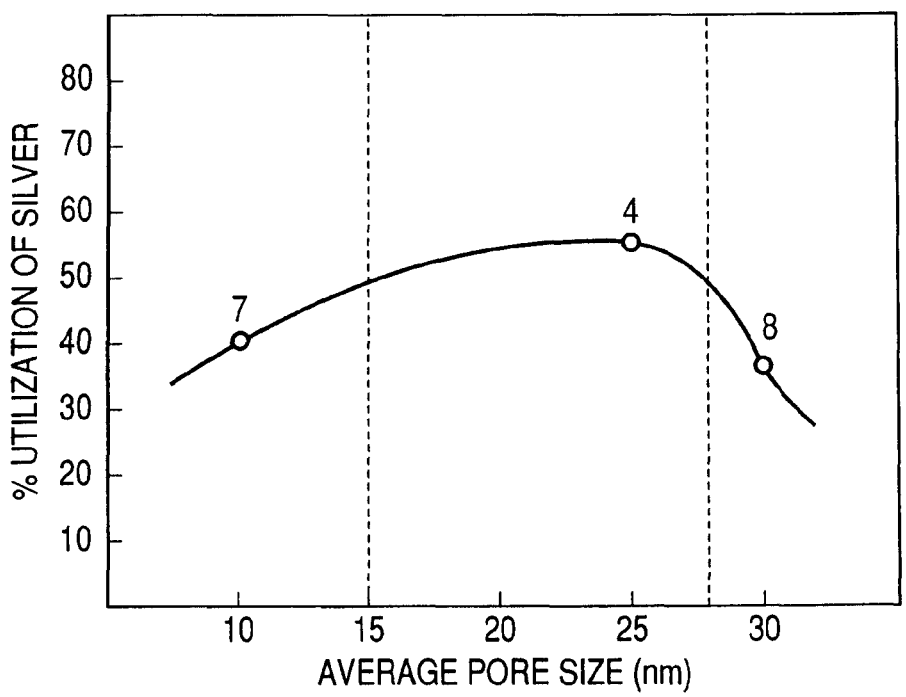
FIG. 3 shows a relationship between a silver utilization and an average pore size in an adsorbent.

The result of the above described test 4 and the tests 7 to 8 are shown in FIG. 3. Numeric values noted upside the plotted data are run numbers. It is understood from FIG. 3 that when conditions other than the pore size are approximately the same, resins with a too large average pore size (30 nm) and a too small average pore size (10 nm) give degraded breakthrough time and silver utilization. It is also understood that when the resin has the average pore size in a range of 15 to 28 nm in particular, the silver utilization is about 50% or more.

Figure 4:
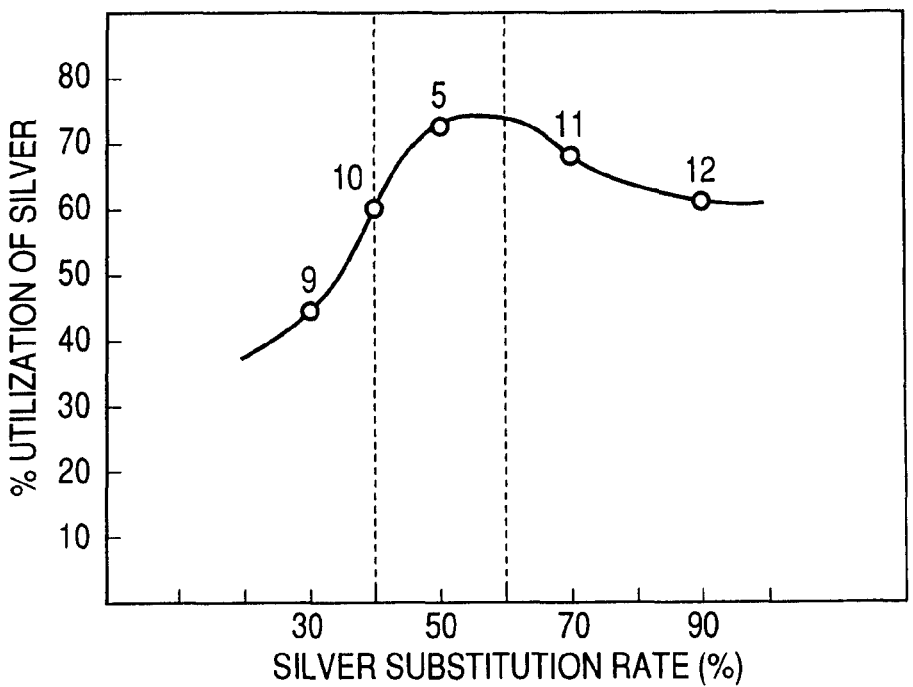
FIG. 4 shows a relationship between a silver utilization and a silver substitution rate in an adsorbent.

The result of the above described test 5 and the tests 9 to 12 are shown in FIG. 4. Numeric values noted upside the plotted data are run numbers. It is understood from FIG. 4 that a silver utilization increases along with the increase of a silver substitution rate before the silver substitution rate reaches 50%, but the silver utilization contrarily decreases after the silver substitution rate has exceeded 60%.

This application claims the benefit of Japanese Patent Application No. 2006-258437, filed Sep. 25, 2006, which is incorporated by reference herein in its entirety.

The invention claimed is:

1. A method for adsorbing and removing an iodide compound from an organic acid containing the iodide compound as an impurity by passing the organic acid through a packed bed of a cation-exchange resin having silver ion carried thereon at 50° C. or lower, wherein the cation-exchange resin is a macroporous-type resin with an average particle size of 0.3 to 0.6 mm and an average pore size of 15 to 28 nm, and silver substitutes for 40 to 60% of the active sites.

2. The method according to claim 1, wherein the organic acid is acetic acid.

3. The method according to claim 1, wherein the iodide compound is an alkyl iodide having 1 to 12 carbon atoms or a mixture thereof.

* * * * *